United States Patent
Chung et al.

(10) Patent No.: US 8,751,495 B2
(45) Date of Patent: Jun. 10, 2014

(54) AUTOMATED PATIENT/DOCUMENT IDENTIFICATION AND CATEGORIZATION FOR MEDICAL DATA

(75) Inventors: Stanley Chung, Royersford, PA (US); Faisal Farooq, King of Prussia, PA (US); Glenn Fung, Madison, WI (US); Balaji Krishnapuram, King of Prussia, PA (US); R. Bharat Rao, Berwyn, PA (US); Romer E. Rosales, Downingtown, PA (US); John Weis, Collegeville, PA (US); Shipeng Yu, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/891,983

(22) Filed: Sep. 28, 2010

(65) Prior Publication Data
US 2011/0078145 A1 Mar. 31, 2011

Related U.S. Application Data

(60) Provisional application No. 61/246,658, filed on Sep. 29, 2009.

(51) Int. Cl.
G06F 7/00 (2006.01)
G06F 17/00 (2006.01)
G06F 17/30 (2006.01)

(52) U.S. Cl.
CPC .............................. *G06F 17/30616* (2013.01)
USPC ............................ 707/737; 707/748; 707/802

(58) Field of Classification Search
USPC ............ 707/713; 705/64; 704/1, 257; 706/12
See application file for complete search history.

(56) References Cited

U.S. PATENT DOCUMENTS

| | | | |
|---|---|---|---|
| 5,738,102 | A | 4/1998 | Lemelson |
| 5,809,476 | A | 9/1998 | Ryan |
| 5,935,060 | A | 8/1999 | Iliff |
| 6,081,786 | A | 6/2000 | Barry et al. |
| 6,212,526 | B1 | 4/2001 | Chaudhuri et al. |
| 6,295,543 | B1 | 9/2001 | Block et al. |
| 6,468,210 | B1 | 10/2002 | Iliff |
| 6,523,019 | B1 | 2/2003 | Borthwick |
| 6,551,243 | B2 | 4/2003 | Bocionek et al. |
| 6,551,266 | B1 | 4/2003 | Davis, Jr. |
| 6,587,829 | B1 | 7/2003 | Camarda et al. |
| 6,641,532 | B2 | 11/2003 | Iliff |

(Continued)

OTHER PUBLICATIONS

Kamp, et al. "Database system support for multidimensional data analysis in environmental epidemiology", The 1997 International Database Engineering & Applications Symposium; Montreal; Can; Aug. 25-27, 1997. pp. 180-188. 1997.

(Continued)

*Primary Examiner* — Susan Chen
(74) *Attorney, Agent, or Firm* — Joshua B Ryan

(57) ABSTRACT

A method, including receiving a data source selection from a user or software application, the data source including medical information of a plurality of patients, receiving, from the user or software application, a data pattern that is related to a concept to be explored in the data source, querying the data source to find information that approximately matches the data pattern; and receiving the information from the data source, wherein the information includes unstructured data, assigning a classification to individual parts of the information based on the part's relationship to the data pattern, and outputting the classified information to the user or software application.

19 Claims, 6 Drawing Sheets

| Passage | Classification/Label | |
|---|---|---|
| 301a The patient <u>exercises</u> daily | In favor | 302a |
| 301b The patient normally follows a 30 min <u>jogging/walking</u> routine | In favor | 302b |
| 301c The patient fails to <u>exercise</u> daily | Against | 302c |
| 301d While <u>daily activity</u> was recommended, the patient normally ignores it | Against | 302d |
| 301e There has been a mild increase in <u>physical activity</u>, but this is still insufficient for this patient's needs | In favor (weak evidence) | 302e |

(56) References Cited

U.S. PATENT DOCUMENTS

| | | | |
|---|---|---|---|
| 6,903,194 B1 | 6/2005 | Sato et al. | |
| 7,130,457 B2 | 10/2006 | Kaufman et al. | |
| 7,340,466 B2 * | 3/2008 | Odom et al. | 1/1 |
| 7,593,605 B2 | 9/2009 | King et al. | |
| 7,633,493 B2 | 12/2009 | Syeda-Mahmood et al. | |
| 7,657,521 B2 | 2/2010 | Masarie et al. | |
| 7,716,072 B1 | 5/2010 | Green, Jr. et al. | |
| 7,805,377 B2 * | 9/2010 | Felsher | 705/64 |
| 7,812,935 B2 | 10/2010 | Cowburn et al. | |
| 7,850,069 B2 | 12/2010 | Taniguchi et al. | |
| 7,899,764 B2 * | 3/2011 | Martin et al. | 706/12 |
| 7,936,925 B2 | 5/2011 | Martin et al. | |
| 8,000,956 B2 | 8/2011 | Brun et al. | |
| 8,108,381 B2 * | 1/2012 | Eberholst et al. | 707/713 |
| 2003/0036683 A1 | 2/2003 | Kehr et al. | |
| 2003/0046114 A1 | 3/2003 | Davies et al. | |
| 2003/0120133 A1 | 6/2003 | Rao et al. | |
| 2003/0120134 A1 | 6/2003 | Rao et al. | |
| 2003/0120514 A1 | 6/2003 | Rao et al. | |
| 2003/0120516 A1 | 6/2003 | Perednia | |
| 2003/0125984 A1 | 7/2003 | Rao et al. | |
| 2003/0125985 A1 | 7/2003 | Rao et al. | |
| 2003/0125988 A1 | 7/2003 | Rao et al. | |
| 2003/0126101 A1 | 7/2003 | Rao et al. | |
| 2003/0130871 A1 | 7/2003 | Rao et al. | |
| 2005/0182656 A1 | 8/2005 | Morey | |
| 2006/0007189 A1 | 1/2006 | Gaines, III et al. | |
| 2006/0020444 A1 * | 1/2006 | Cousineau et al. | 704/1 |
| 2006/0020466 A1 * | 1/2006 | Cousineau et al. | 704/257 |
| 2006/0059162 A1 | 3/2006 | Rizk et al. | |
| 2006/0173679 A1 | 8/2006 | DelMonego et al. | |
| 2007/0050187 A1 | 3/2007 | Cox | |
| 2008/0059228 A1 | 3/2008 | Bossi et al. | |
| 2009/0006126 A1 | 1/2009 | Champigny | |
| 2009/0192800 A1 | 7/2009 | Brandt | |
| 2009/0222354 A1 | 9/2009 | Murphy et al. | |
| 2010/0094657 A1 | 4/2010 | Stern et al. | |
| 2010/0331043 A1 | 12/2010 | Chapman et al. | |
| 2011/0202370 A1 | 8/2011 | Green, III et al. | |

OTHER PUBLICATIONS

King, et al., "MEDUS/A: Distributing Database Management for Medical Research", Proceedinngs of Computer Networks Compcon 82, Sep. 20-23, 1982 pp. 635-642.

Boxwala et al, "Architecture for a Multipurpose Guideline Execution Engine", Proc. AMIA Symp 1999, pp. 701-705.

"Guidance for Institutional Review Boards and Clinical Investigators 1998 Update", Sep. 1998, U.S. Food and Drug Administration, http://www.fda.gov/ScienceResearch/SpecialTopics/RunningClinicalTrials/GuidancesInformationSheetsandNotices/ucm113793.htm#IRBMember.

Kassirer, "The Use and Abuse of Practice Profiles", The New England Journal of Medicine, vol. 330:634-636, Mar. 3, 1994.

Chen, et al., Do "America's Best Hospitals" Perform Better for Acute Myocardial Infarction?, The New England Journal of Medicine, vol. 340, No. 4:286-292, Jan. 28, 1999.

Hofer, et al., "The Unreliability of Individual Physician 'Report Cards' for Assessing the Costs and Quality of Care of a Chronic Disease", JAMA, Jun. 9, 1999, vol. 281, No. 22, pp. 2098-2105.

Ong et al, "The Colorectal Cancer Recurrence Support (CARES) System; Artificial Intelligence in Medicine", Nov. 1997, Elsevier, Netherlands, vol. 11, pp. 175-188.

Nahm, et al., "A Mutually Beneficial Integration of Data Mining and Information Extraction", In Proceedings of the Seventeenth National Conference on Artificial Intelligence (AAAI-2000), Jul. 30, 2000, pp. 627-632, Austin, TX, 20001.

Rao, et al., "Data mining for disease management: adding value to patient records", Electromedica, vol. 68, 2000, pp. 63-67.

Mills, "Computer Technology of the Not-Too-Distant Future" Sep. 1993, Medical Laboratory Observer, vol. 25, No. 9, p. 78.

Duda, et al., "Pattern Classification—Chapter 1" 2001, John Wiley & Sons, New York, US, XP002536377, pp. 14-17.

Hudson, et al., "The Feasibility of Using Automated Data to Assess Guideline-Concordant Care for Schizophrenia", Journal of Medical Systems, vol. 23 No, 4 1999, pp. 299-307.

PR Newswire, "Diabetes Health Management Award Honors Mayo Clinic's Zimmerman", Sep. 25, 2000, http://www.thefreelibrary.com/Diabetes Health Management Award Honors Mayo Clinic's Zimmerman.-a065465402.

Hudson, Mary E., "CAATS and compliance—computer-assisted audit techniques in health care", Internal Auditor, Apr. 1998, vol. 55, No. 2, p. 25, http://findarticles.com/p/articles/mi_m4153/is_n2_v55/ai_20860208/.

Grimes, Seth, "Structure, Models and Meaning, Is 'Unstructured' data merely unmodeled?", Intelligent Enterprise, Mar. 2005, http://intelligent-enterprise.informationweek.com/showArticle.jhtml?articleID=59301538.

Berkus, "Unstructured Data as an Oxymoron", ITtoolbox Blogs, Sep. 1, 2005, http://it.toolbox.com/blogs/database-soup/unstructured-data-as-an-oxymoron-5588.

Larsen, "Fast and Effective Test Mining Using Linear-time Document Clustering", In Knowledge Discovery and Data Mining (1999), pp. 16-22.

Rao, "From Unstructured Data to Actionable Intelligence", IT Pro, Nov./Dec. 2003, pp. 29-35.

Mitchell, "Machine Learning and Data Mining", Communications of the ACM, Nov. 1999, vol. 42, No. 11, pp. 31-36.

Kleissner, "Data Mining for the Enterprise", System Sciences, 1998, Proceedings of the Thirty-First Hawaii International Conference on Kohala Coast, HI, Jan. 6-9, 1998, IEEE Comput. Soc. US, pp. 295-304.

Evans, et al., "Using Data Mining to Characterize DNA Mutations by Patient Clinical Features", Proc AMIA Annu Fall Symp. 1997: 253-257.

Waltz, "Information Understanding Integrating Data Fusion and Data Mining Processes", Circuits and Systems, 1998, Proceedings of the 1998 IEEE International Symposium in Monterey, CA, USA, May 31-Jun. 3, 1998, NY, NY, May 31, 1998, pp. 553-556.

Roemer, et al., "Improved diagnostic and prognostic assessments using health management information fusion," AUTOTESTCON Proceedings, 2001. IEEE Systems Readiness Technology Conference , vol., no., pp. 365-377, 2001.

Chemical and Biological Arms Control Institute: "Bioterrorism in the United States:Threat, Preparedness and Response", Contract No. 2001*1999*00132, Nov. 2000.

Hanson, et al.. "Probabilistic Heuristic Estimates", Annals of Mathematics and Artificial Intelligence, vol. 2, Nos. 1-4, pp. 209-220, 1990.

Anquetil et al. "Integration of an on-line handwriting recognition system in a smart phone device." 16th International Conference on Pattern Recognition [Online] 2002, vol. 3, pp. 192-195. (See abstract).

Carbonnel et al. "Lexical post-processing optimization for handwritten word recognition." Seventh International Conference on Document Analysis and Recognition [Online] 2003, vol. 1, pp. 477-481. (See abstract).

Plamondon et al. "Handwritten sentence recognition: from signal to syntax." Proceedings of the 12th IAPR International Conference on Pattern Recognition [Online] 1994, vol. 2, pp. 117-122. (See abstract).

Taylor et al. "Advances in interactive video scanning of paper documents." IEE Colloquium on Document Image Processing and Multimedia [Online] 1999, pp. 1/1-1/5. (See abstract).

Faisal Farooq "Language Models and Automatic Topic Categorization for Information Retrieval in Handwritten Documents." Dissertation Submitted to the Faculty of the Graduate School of State University of New York at Buffalo, May 2008.

Koerich et al. "Large vocabulary off-line handwriting recognition: A survey." Pattern Anal Applic 2003, 6: pp. 97-121.

Cutler et al. "U.S. Adoption of Computerized Physician Order Entry Systems." DataWatch 2005, pp. 1654-1663.

* cited by examiner

| Passage | Classification/ Label |
|---|---|
| The patient exercises daily | In favor |
| The patient normally follows a 30 min jogging/walking routine | In favor |
| The patient fails to exercise daily | Against |
| While daily activity was recommended, the patient normally ignores it | Against |
| There has been a mild increase in physical activity, but this is still insufficient for this patient's needs | In favor (weak evidence) |

| Matched | Type | AfibAflutterSC | TEST2AfibAflutter |
|---|---|---|---|
| THYROID ABLATION | THYROID SCAN | N/A | -0.8704031695443 |
| endometrial ablation | HIST/PHYSCL | N/A | -1.2430359740971 |
| NovaSure | HIST/PHYSCL | N/A | -0.5538033412694 |
| ATRIAL FIBRILLATION | DISCHARGE SM | Yes | 1.2043601641278 |
| CRYOABLATION | DIAGNOSIS | N/A | -0.8197962397088 |
| cryoablation | DIAGNOSIS | N/A | -0.7612600505743 |
| ATRIAL FIBRILLATION | CONSULTATION | Yes | 1.1569062512464 |
| ATRIAL FIBRILLATION | HIST/PHYSCL | Yes | 0.8420755717377 |
| CABG IN 2002 WITH THE LIMA TO LAD ANI | Cardiac Cath | Yes | 0.6543438039678 |
| ATRIAL FIBRILLATION | CONSULTATION | Yes | 0.9248502360349 |
| NO OTHER DOCUMENTED ATRIAL FIBRILL | HIST/PHYSCL | Yes | 0.3312025354614 |
| ATRIAL FIBRILLATION | CONSULTATION | Yes | 1.1591575595724 |
| ATRIAL FIBRILLATION | HIST/PHYSCL | Yes | 0.9083567007128 |
| ATRIAL FIBRILLATION | HIST/PHYSCL | Yes | 0.8521341808389 |
| ATRIAL FIBRILLATION | DISCHARGE SM | Yes | 1.7888392989748 |
| CABG IN 2004. 8. NEW ONSET OF ATRIAL | DISCHARGE SM | Yes | 0.9958845478205 |
| ATRIAL FIBRILLATION | HIST/PHYSCL | Yes | 1.0154454700510 |
| atrial fibrillation | DISCHARGE SM | Yes | 1.0855312996930 |
| NOVASURE | HIST/PHYSCL | N/A | -0.6189147630283 |
| CABG SUSTAINED ATRIAL FIB | DISCHARGE SM | Yes | 0.4101741614111 |
| AFIB | CONSULTATION | Yes | 0.0366685434171 |
| no evidence of atrial fibrillation | CONSULTATION | No | -0.6672465470190 |
| no evidence of atrial fib | CONSULTATION | No | -0.6672465470190 |
| NO EVIDENCE OF ATRIAL FIBRILLATION | HIST/PHYSCL | No | -1.3113431496878 |
| NO EVIDENCE OF ATRIAL FIB | HIST/PHYSCL | No | -1.3113431496878 |
| ATRIAL FIBRILLATION | HIST/PHYSCL | Yes | 1.1727385777469 |
| coronary sinus. Further mapping was perfc | Cardiac Vasc | Yes | 0.5069764718514 |
| NO EPISODES OF ATRIAL FIB/ATRIAL FLUT | CONSULTATION | No | 0.0975117799858 |
| ATRIAL FIBRILLATION | HIST/PHYSCL | Yes | 0.8779973922293 |
| THYROID ABLATION | THYROID SCAN | N/A | -0.7355061518282 |
| ATRIAL FIBRILLATION | CONSULTATION | Yes | 0.7037833119204 |

Displaying passages 1 - 100 of 285

FIG. 5B

AUTOMATED PATIENT/DOCUMENT IDENTIFICATION AND CATEGORIZATION FOR MEDICAL DATA

CROSS-REFERENCE TO RELATED APPLICATION

This application claims priority under 35 U.S.C. §119 to U.S. Provisional Application No. 61/246,658, filed Sep. 29, 2009, the disclosure of which is incorporated by reference herein in its entirety.

BACKGROUND OF THE INVENTION

1. Technical Field

The present invention relates to extracting and classifying medical data from a medical data storage source, and more particularly, to extracting and classifying medical data that is in unstructured form from such a source.

2. Discussion of the Related Art

In general, an electronic medical record (EMR) is a computerized legal medical record created in an organization that delivers care, such as a hospital or doctor's office. In an EMR, various data elements may be associated to a patient or a patient visit; for example, diagnosis codes, lab results, pharmacy, insurance, doctor notes, radiological images, genotypic information, etc. EMRs tend to be part of a local stand-alone health information system that allows storage, retrieval and manipulation of records.

Data in an EMR is stored in structured or unstructured form. FIG. 1 shows an exemplary EMR 100 with structured and unstructured data. In FIG. 1, the patient's name "John Doe" in field 110 and the examination date "Jan. 1, 2007" in field 120 are examples of structured data. The medical report (e.g., doctor's note) "Patient presents . . . " in field 130 is an example of unstructured data. Other examples of structured data may include date of birth (mm/dd/yyyy), zip code (a five-digit number), smoke status (either yes/no), insurance type (either medicare/medicade/private), or medication list (medication A, medication B . . . ). Other examples of unstructured data may include images, lab reports, biological sequences and other forms of written reports.

The distinction between these two data types is that desired information can be easily extracted from structured data by using a standard database query language, such as Structured Query Language (SQL). This is so, because the format of the structured data is generally fixed and already known. In contrast, it is not easy to extract desired information from unstructured data. This is so, because the format of the unstructured data is generally not fixed or it is too generic.

For example, with reference to FIG. 1, it is straightforward for a computer to determine the patient's name from the name of patient field 110, or the date of the patient's examination from the date of examination field 120, in both cases assuming the computer knows the formatting of fields 110 and 120. However, due to the freeform entry of data into the medical report field 130, it is not straightforward for a computer to determine what the patient's prescription is from field 130.

As can be gleaned, unstructured data is an essential source of patient information. In fact, it is widely accepted that key clinical information in an EMR is stored in unstructured form. However, by their inherent nature discussed above, it is difficult to automatically extract useful information contained in unstructured data and make it available in a readily usable form. Such information is typically found through manual search.

SUMMARY OF THE INVENTION

In an exemplary embodiment of the present invention, there is provided a method comprising: receiving a data source selection from a user or software application, the data source including medical information of a plurality of patients; receiving, from the user or software application, a data pattern that is related to a concept to be explored in the data source; querying the data source to find information that approximately matches the data pattern; and receiving the information from the data source, wherein the information includes unstructured data, assigning a classification to individual parts of the information based on the part's relationship to the data pattern, and outputting the classified information to the user or software application, and wherein the method is performed using a processor.

The classified information is arranged in tabular form with a row containing an individual part of the information in one column and the part's classification in another column.

The row further includes a link to the source containing the individual part of the information.

The row further includes a numerical score indicating a strength of the classification.

The method further comprises grouping individual parts of the information in adjacent rows, wherein the grouping is based on similarity of the individual pails to each other.

An unstructured data search algorithm is used to find the information that approximately matches the data pattern.

The data source includes electronic medical records, radiological images, or gene sequences.

The unstructured data includes text, images or biological sequences.

The classified information includes structured data.

The concept is a medical question.

The data pattern includes a keyword, regular expression or a context-free grammar.

The data pattern includes an image part or an image filter.

The data pattern includes genetic data.

In an exemplary embodiment of the present invention, there is provided a system comprising: a memory device for storing a program; a processor in communication with the memory device, the processor operative with the program to: receive a data source selection, the data source including medical information of a plurality of patients; receive a data pattern that is related to a concept to be explored in the data source; query the data source to find information that approximately matches the data pattern; and receive the information from the data source, wherein the information includes unstructured data assign a classification to individual parts of the information based on the part's relationship to the data pattern, and output the classified information.

The classification indicates when the individual part of the information is positive, negative or not applicable to the data pattern.

The processor is further operative with the program to display the output on a graphical user interface (GUI).

The classified information is browsable, editable, or processible via the GUI.

In an exemplary embodiment of the present invention, there is provided a computer program product comprising: a non-transitory computer readable storage medium having computer readable program code embodied therewith, the computer readable program code comprising: computer readable program code configured to perform the steps of: querying a data source to find data that exactly or approximately matches a data pattern, wherein the data source includes medical information of a plurality of patients; and receiving the data from the data source, wherein the data includes unstructured data, assigning a classification or score to individual parts of the data based on the part's relationship to the data pattern, and outputting the classified/scored data.

The data source or the data pattern is pre-determined.

The data pattern is determined from a concept, the concept being related to a medical question

BRIEF DESCRIPTION OF THE DRAWINGS

FIG. 3 is a table illustrating an exemplary output of the present invention;

FIGS. 5A and 5B are part of the same screen-shot that illustrates an exemplary output of the present invention.

DETAILED DESCRIPTION OF EXEMPLARY EMBODIMENTS

Disclosed herein, in accordance with an exemplary embodiment of the present invention, is a method of automatically extracting and classifying medical data from a medical data storage source, in particular, unstructured medical data. In using this method, medical personnel can find desired information in the unstructured data without having to perform a manual search, for example. Further, in this method, the extracted information may be classified based on whether it matches the medical personnel's input criteria positively or negatively (or some other matching level as described below).

Figure 1:
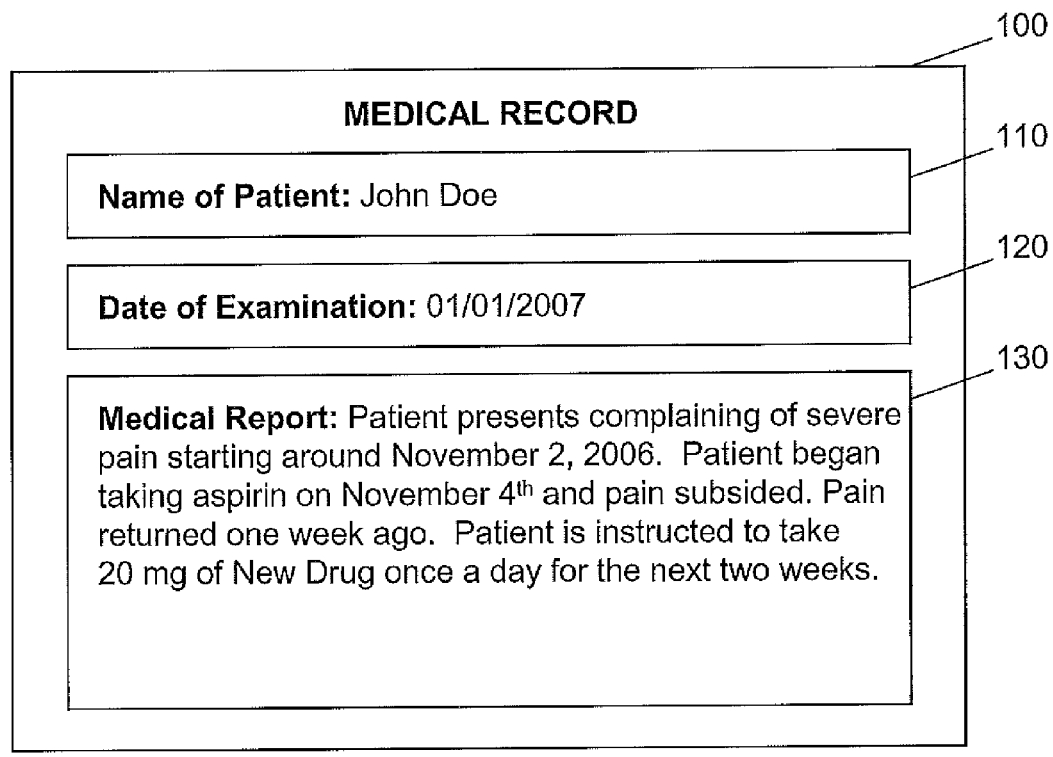
FIG. 1 is an exemplary electronic medical record (EMR) including structured and unstructured data.
Figure 2:
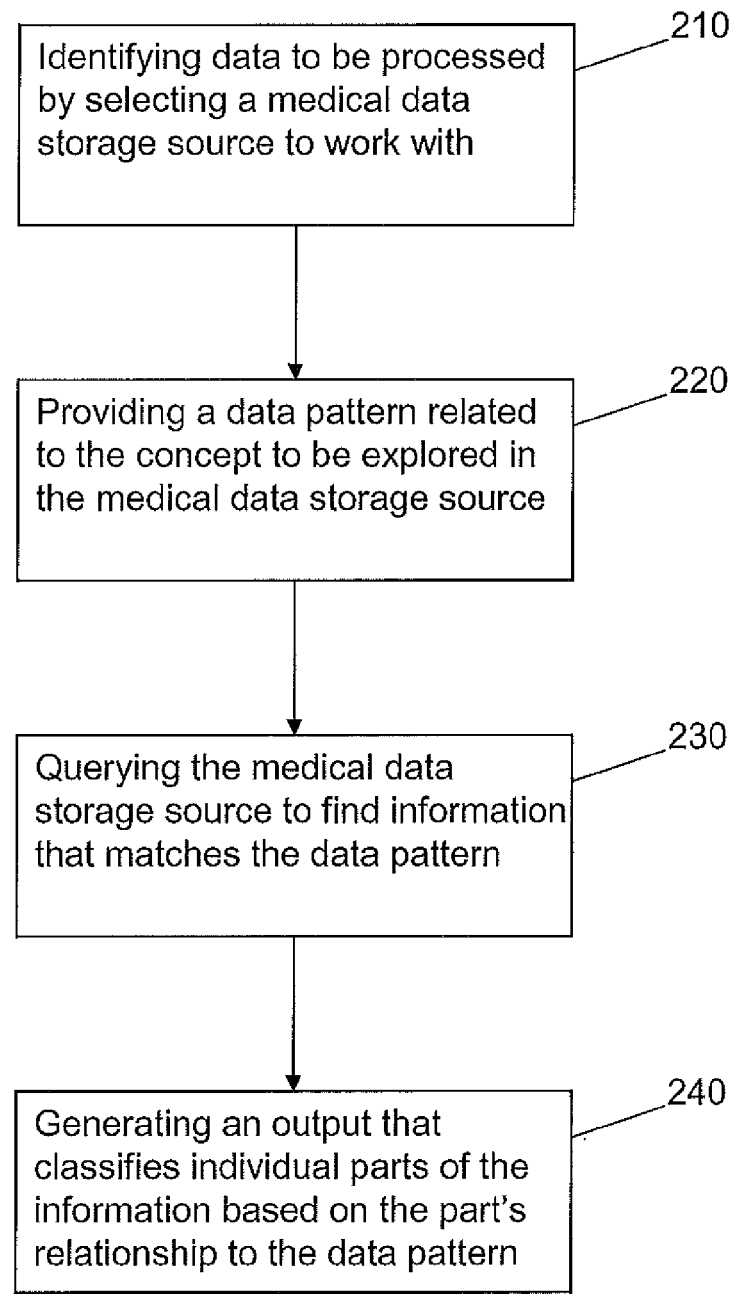
FIG. 2 is a flowchart illustrating an exemplary embodiment of the present invention.

FIG. 2 is a flowchart illustrating a method of automatically extracting and classifying medical data from a medical data storage source according to an exemplary embodiment of the present invention.

As shown in FIG. 2, data to be processed is identified (210). This may include selecting a specific medical data storage source, subset of data based on time, date, document type, or any other available attribute. This information may be provided by a user or an external application. For example, a user may select one or more medical data storage sources to work with. The selection may be made through a computer's user interface by providing the user with a number of such sources from which to choose. A software application equipped with Siemens' REMIND™ technology or a system such as Siemens' SOARIAN® Quality Measures can be used to automatically identify the data to be processed. For example, SOARIAN® Quality Measures can be configured to connect to certain databases within a hospital by default or in response to a certain type of request.

The medical data storage sources may include, but are not limited to, a hospital information system that is a comprehensive, integrated information system designed to manage the administrative, financial and clinical aspects of a hospital, a lab information system that receives, processes and stores information generated by medical laboratory processes, and a radiology information system that enables storage, manipulation and distribution of patient radiological data and imagery.

The user or external application may then provide a data pattern related to a concept to be searched in the medical data storage source (220). A concept to be searched may be related to a medical question or medical concept such as "Does the patient currently smoke?", "Did the patient stop smoking during the year prior to hospital admission?", "Was the patient given instructions on follow-up after discharge?", "Does the patient exercise regularly?", or "Does the patient live in a home care environment?"

For example, for the medical concept "Does the patient exercise regularly?", the data pattern may be the following three keywords: "exercise, sport, activity," entered by the user. In a system implementing an exemplary embodiment of the present invention, additional keywords or phrases for this example can be suggested such as "aerobic exercise, running, jogging, walking, physical activity, daily activity." This can be done based on pre-configured or automatically gathered data. In other words, if the original keyword was "smoke," the terms "smoking history" or "positive for tobacco use" can be suggested by the system, if these terms are prevalent in the data source. Additional keywords that have a high co-occurrence with the keywords that the user provides might also be suggested.

An external application could also be preconfigured to select its own keywords. For example, a software application could employ an algorithm that generates its own keywords based on data currently being processed or displayed by the application. In other words, if the software application is processing customer data and sees repeated occurrences of the words "smoke" and "history," the application could make its own query that is a combination of these two words.

For the case of unstructured text, the data pattern can be a keyword, or a regular expression written in a formal language that can be interpreted by a regular expression processor. In addition, the data pattern can be a context-free grammar. For the case of unstructured images, the data pattern can be an image filter (e.g., a sub-image from within an image that contains something a user wants to find in other images), a convolution operator, or an image matching pattern that aims to find images that have similar intensities or similar responses to soft filters. For the case of unstructured biological sequences, the data pattern can be a gene expression profile. For example, the data pattern can be configured as a request to find gene subsequences that contain a particular gene.

The system may then query the available data to identify passages, documents, or patients that match the search criteria (230). In other words, the medical data storage source is queried to find information that matches the data pattern. A variety of unstructured data search algorithms may be used in this step such as sequential search (where the source is explored sequentially), indexed search (where the source has been previously indexed according to an index criterion), or partial search (where only some parts of the source are explored).

A data pattern may be matched exactly or approximately. By approximately, it is meant that the data pattern matches the found information to a given extent (e.g., above a certain threshold, percentage/probability, or filter response value). Approximate matching can also be based on automatically expanding the search criteria to provide results that are deemed relevant based on the data and past experience, but do not exactly match the keywords provided by the user. This can be done to account for variations in the way the same concept can be represented or stated, e.g., one doctor may refer to a patient as a "smoker," whereas another doctor may refer to a patient as a "tobacco user." The automatic expansion of the search criteria can be achieved by training statistical models and natural language processing systems.

The system may then produce a result (e.g., organized data) that indicates which patient, documents, or passages matched the search criteria positively or negatively or some other matching level (240). In other words, the system generates an output that classifies individual parts of the information based on the part's relationship to the data pattern. For example, the system automatically divides the matches into those that provide evidence in favor of the keywords, against the keywords, or that are neutral/weak to the keywords. Table 300 in FIG. 3 shows an example of this.

In particular, table 300 represents the result of the identification and classification of unstructured data fragments based on the query: "exercise, sport, activity." In table 300, the rows under the "Passage" column-header include matching unstructured data fragments 301a-e, and the rows under the "Classification/Label" column-header include the unstructured data fragment's relationship to the query 302a-e. As further shown in table 300, words corresponding to the query in the unstructured data are underscored to make it easy for a user to see them.

As can be seen, the information organized in table 300 can be used to identify patients that exercise or do not exercise (or some intermediate classification). The information can also be used to retrieve the documents that include the displayed passages. These documents could also be classified as documents indicating that the patient exercises or not. For example, the unstructured data fragments 301a-e could be linked to the EMRs from where they reside. In addition to the classification or label as shown in table 300, a numerical score indicating the strength of the classification or label may also be provided. This may be achieved by identifying negations/modifications of search terms and concepts based on the linguistic information (e.g., structure and grammar) as provided by natural language systems.

In the example shown in FIG. 3, "exercise" can be regard as the general concept of interest. Other keywords to be searched in the example of FIG. 3 may include "follow-up instructions" or "smoking." The labels "against," "in favor" or other intermediate levels may be regarded as the concept labels or classifications.

The concept labels or classifications can be defined in multiple ways. For example, for the "exercise" example above, an alternative classification such as "daily," "three times a week," "weekly," "never" can be used. This can be achieved by training a machine learning classifier, natural language processing system, or statistical model, and thus there is no strong limit on what label names/categories can be used beyond that given by the available data or in the domain knowledge. In addition, multiple concepts (and their classifications) can be grouped together in order to, for example, identify patients that satisfy multiple criteria (e.g., smoke and do not exercise). Algorithmically, the classification can be achieved in multiple ways.

The information obtained in step 240 can also be displayed to a user for browsing, correcting, and editing. In addition, the information obtained can be grouped (e.g., aggregated) based on similarity in the passages that are retrieved for ease of browsing and performing other tasks such as, but not limited to, editing, statistical analysis, etc. This can be achieved by training machine learning classifiers in conjunction with natural language processing to evaluate passage similarity.

Structured data can also be used in conjunction with the unstructured data, and thus included in table 300. This can be done by considering the structured data as additional information.

Figure 4:
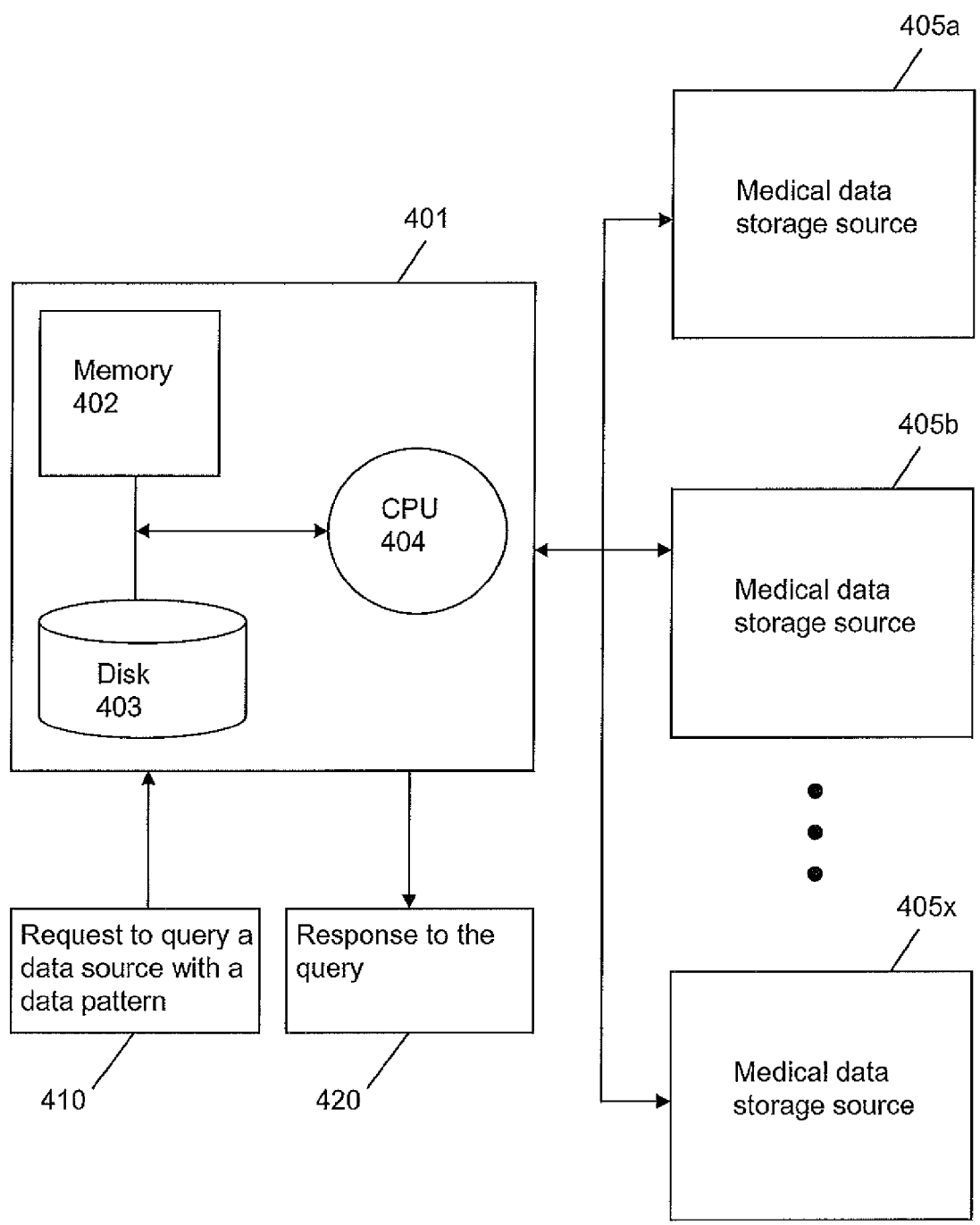
FIG. 4 is a computer system in which an exemplary embodiment of the present invention may be implemented.

An exemplary embodiment of the present invention will now be described with reference to apparatus 401 in FIG. 4.

The apparatus 401, which may be a computer, includes a memory 402, a disk 403, and a processor such as a central processing unit (CPU) 404. The apparatus 401 may be connected to a plurality of medical data storage sources 405a-x via a wired or wireless network. The medical data storage sources 405a-x may be one of the medical data storage sources mentioned above.

It is to be understood that the term "processor" as used herein is intended to include any processing device, such as, for example, one that includes a CPU and/or other forms of processing circuitry. Further, the term "processor" may refer to more than one individual processor. The term "memory" is intended include memory associated with a processor or CPU, such as, for example, random access memory (RAM), read only memory (ROM), a fixed memory device (for example, hard drive), a removable memory device (for example, diskette), a flash memory and the like. In addition, the phrase "input and/or output interface" as used herein, is intended to include, for example, one or more mechanisms for inputting data to the processing unit (for example, mouse), and one or more mechanisms for providing results associated with the processing unit (for example, printer).

In some embodiments, a request to query a particular medical data storage source 405a-x with a data pattern 410 may be input to apparatus 401, such as a search request that is input from a user. For example, the search request may include the following keywords "Atrial Fibrilation" and "Flutter" and a particular database to be searched input in a manner discussed above. In some embodiments, a response 420 to the request is output from the apparatus 401. The response 420 is generated according to the processes described above.

Figure 5A:
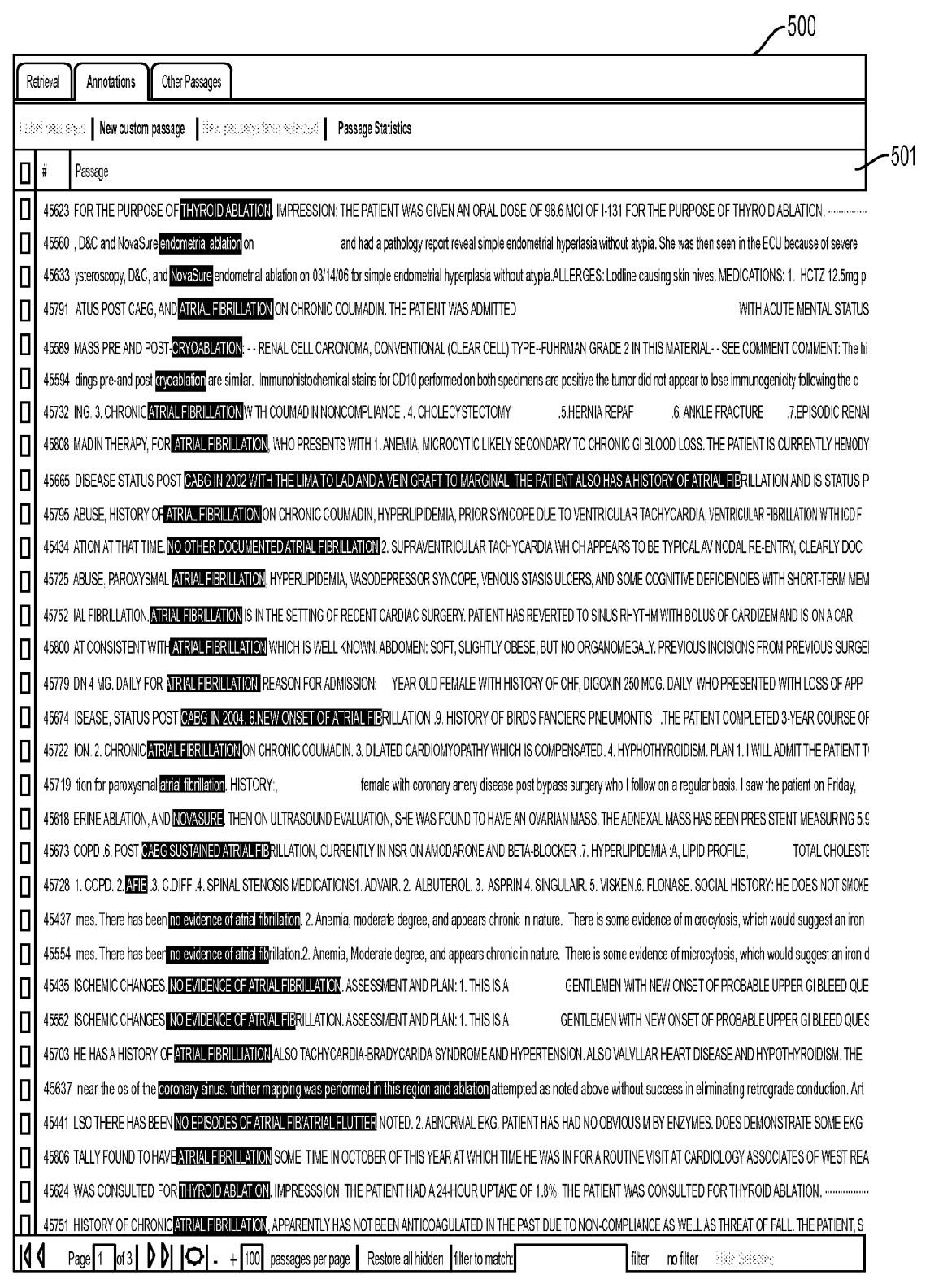

FIGS. 5A and 5B illustrate an exemplary response 500 output from the apparatus 401 in response to the "Atrial Fibrilation" and "Flutter" query. In FIG. 5A, the unstructured data fragment passages are listed in column 501 and the matching terms are highlighted. In FIG. 5B, column 502 lists the matching terms for ease of reference, column 503 indicates when evidence in the passage is positive, negative or not applicable (even though the keyword search matched the text) to Atrial Fibrilation and Flutter, and column 504 contains a score indicating the strength of the evidence in the data in column 503. This value could also indicate the probability of the evidence. For example, the probability that the evidence is positive is 0.7, negative is 0.2, and not applicable 0.1.

As can be seen, the functionality provided by the exemplary embodiments goes beyond that provided by standard search engines in various manners. In particular, the embodiments enable a higher-level categorization of the text found by assigning classification/labels that can help identify, for example, negative vs. positive findings, various evidence levels, etc.

In an exemplary embodiment, the present invention may be implemented in software as an application program tangibly embodied on a program storage device (e.g., magnetic floppy disk, RAM, compact disk read (CD) ROM, digital video disk (DVD), ROM, and flash memory). The application program may be uploaded to, and executed by, a machine comprising any suitable architecture.

It is to be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

While the present invention has been described in detail with reference to exemplary embodiments thereof, those skilled in the art will appreciate that various modifications and substitutions can be made thereto without departing from the spirit and scope of the present invention as set forth in the appended claims.

What is claimed is:

1. A method, comprising:
receiving a data source selection from a user or software application, the data source including medical information of a plurality of patients;
receiving, from the user or software application, a data pattern that is related to a concept to be explored in the data source;
querying the data source to find information that approximately matches the data pattern; and
receiving the information from the data source, wherein the information includes unstructured data, assigning a classification to individual parts of the information based on the part's relationship to the data pattern; and
outputting the classified information, including the unstructured data as a table including a classification label and a passage header columns, to the user or software application, the passage column being of the unstructured data separated into the individual parts, the unstructured data of the passage column comprising fragment passages that are one or more sentences, one or more clauses, or one or more sentences and clauses, which include a query term and surrounding text, and the classification label indicating positive or negative or not applicable to support of corresponding passages of the passage column and
wherein the method is performed using a processor.

2. The method of claim 1, wherein the row further includes a link to the source containing the individual part of the information.

3. The method of claim 1, wherein the row further includes a numerical score indicating a strength of the classification.

4. The method of claim 1, further comprising grouping individual parts of the information in adjacent rows, wherein the grouping is based on similarity of the individual parts to each other.

5. The method of claim 1, wherein an unstructured data search algorithm is used to find the information that approximately matches the data pattern.

6. The method of claim 1, wherein the data source includes electronic medical records, radiological images, or gene sequences.

7. The method of claim 1, wherein the unstructured data includes text, or biological sequences.

8. The method of claim 1, wherein the classified information includes structured data.

9. The method of claim 1, wherein the concept is a medical question.

10. The method of claim 1, wherein the data pattern includes a keyword, regular expression or a context-free grammar.

11. The method of claim 1, wherein the data pattern includes an image part or an image filter.

12. The method of claim 1, wherein the data pattern includes genetic data.

13. The method of claim 1, wherein receiving the information comprises receiving the unstructured data for the plurality of patients, outputting comprises outputting the unstructured data for the plurality of patients in the table.

14. A system, comprising:
a memory device for storing a program;
a processor in communication with the memory device, the processor operative with the program to:
receive a data source selection, the data source including medical information of a plurality of patients;
receive a data pattern that is related to a concept to be explored in the data source; query the data source to find information that approximately matches the data pattern; and
receive the information from the data source, wherein the information includes unstructured data, assign a classification to individual parts of the information based on the part's relationship to the data pattern, and output the classified information, including the unstructured data in a table, the table being of the unstructured data separated into the individual parts, the unstructured data of the table comprising fragment passages that are one or more sentences, one or more clauses, or one or more sentences and clauses, which include a query term and surrounding text of a passage column header, and the classified information including a corresponding indication of in favor or against or not applicable to the data pattern in a classification label column header for each of the passages of the table.

15. The system of claim 14, wherein the processor is further operative with the program to display the output on a graphical user interface (GUI).

16. The system of claim 15, wherein the classified information is browsable, editable, or processible via the GUI.

17. A computer program product, comprising:
a non-transitory computer readable storage medium having computer readable program code embodied therewith, the computer readable program code comprising:
computer readable program code configured to perform the acts of:
querying a data source to find data that exactly or approximately matches a data pattern, wherein the data source includes medical information of a plurality of patients; and
receiving the data from the data source, wherein the data includes unstructured data, assigning a classification or score to individual parts of the data based on the part's relationship to the data pattern, and outputting the classified/scored data, including the unstructured data in a table, the table being of the unstructured data separated into the individual parts, the unstructured data of the table comprising fragment passages that are one or more sentences, one or more clauses, or one or more sentences and clauses, which include a query term and surrounding text of a passage column header in the table, and the classification or score of a classification label column header in the table including a corresponding indication of positive, negative or not applicable for each of the fragment passages in the table.

18. The computer program product of claim 17, wherein the data source or the data pattern is pre-determined.

19. The computer program product of claim 17, wherein the data pattern is determined from a concept, the concept being related to a medical question.

* * * * *